United States Patent [19]

Khan et al.

[11] Patent Number: 4,806,358

[45] Date of Patent: Feb. 21, 1989

[54] THERAPEUTIC COMPOSITIONS

[75] Inventors: Karrar A. Khan; John F. Lampard, both of Nottingham, England

[73] Assignee: The Boots Company plc, England

[21] Appl. No.: 925,564

[22] Filed: Oct. 31, 1986

[30] Foreign Application Priority Data

Nov. 15, 1985 [GB] United Kingdom ................ 8528195

[51] Int. Cl.$^4$ ............................................... A61K 9/46
[52] U.S. Cl. ................................... 424/466; 424/494; 514/570
[58] Field of Search ............... 424/464, 466, 489, 499, 424/494; 514/570

[56] References Cited

U.S. PATENT DOCUMENTS

| | | | |
|---|---|---|---|
| 4,289,751 | 9/1981 | Windheuser | 424/466 |
| 4,414,198 | 11/1983 | Michaelson | 424/44 |
| 4,678,661 | 7/1987 | Gergely et al. | 424/466 X |
| 4,687,662 | 8/1987 | Schobel | 424/44 |
| 4,689,218 | 8/1987 | Gazzaniga et al. | 424/43 |
| 4,701,470 | 10/1987 | Heckler | 514/532 X |

FOREIGN PATENT DOCUMENTS

| | | |
|---|---|---|
| 137668 | 4/1985 | European Pat. Off. . |
| 203768 | 12/1986 | European Pat. Off. . |
| 2750207 | 11/1978 | Fed. Rep. of Germany . |
| 2174004 | 4/1985 | United Kingdom . |

OTHER PUBLICATIONS

Scrip.
Chem. Abs., vol. 74 (1971) 76639z.
Derwent 87-144381/21; 86-125895.

Primary Examiner—Michael Lusignan
Attorney, Agent, or Firm—Jacobs & Jacobs

[57] ABSTRACT

Novel pharmaceutical powder and tablet compositions comprise ibuprofen or a pharmaceutically acceptable salt thereof, a pharmaceutically acceptable effervescent couple that produces carbon dioxide in the presence of water, a pharmaceutically acceptable surfactant and a pharmaceutically acceptable water-insoluble hydrophilic polymer. Preferred hydrophilic polymers are microcrystalline cellulose and croscarmellose sodium.

Especially preferred are such compositions which have a saccharide dispersed therein. The incorporation of the saccharide, for example sucrose, lactose, dextrose or sorbitol, enhances the stability of the compositions.

14 Claims, No Drawings

THERAPEUTIC COMPOSITIONS

This invention relates to pharmaceutical compositions of ibuprofen for oral administration. More particularly, the invention relates to pharmaceutical powder and tablet compositions containing ibuprofen or a salt thereof which effervesce when added to water, forming an aqueous suspension of ibuprofen suitable for oral administration. Such aqueous suspensions are convenient in use and are advantageous for those patients, often children and elderly patients, who have difficulty in swallowing tablets or capsules.

Ibuprofen, the chemical name of which is 2-(4-isobutylphenyl)propionic acid, is a well known medicament with anti-inflammatory, antipyretic and analgesic activities. The uses of ibuprofen include the treatment of pain and inflammation in musculoskeletal disorders such as rheumatic disease, and the treatment of pain in a variety of other disorders.

The present invention provides a pharmaceutical powder or tablet composition comprising ibuprofen or a pharmaceutically acceptable salt thereof, a pharmaceutically acceptable effervescent couple that produces carbon dioxide in the presence of water, a pharmaceutically acceptable surfactant and a pharmaceutically acceptable water-insoluble hydrophilic polymer.

The compositions of the present invention effervesce when added to water, producing an aqueous suspension of ibuprofen which can be swallowed by a patient as the effervescence continues.

We have found that the inclusion of the water-insoluble hydrophilic polymer in the compositions of the present invention gives an improved suspension of ibuprofen or salt thereof when the compositions of the present invention are added to water. This has the advantageous result that, when a patient has consumed an aqueous suspension of ibuprofen or salt thereof prepared from a composition of the present invention, only a small amount of particles of ibuprofen or salt thereof is left as a residue on the sides of the drinking vessel used by the patient. In the absence of the water-insoluble hydrophilic polymer, the amount of ibuprofen or salt thereof left as a residue is unacceptale large and is also more variable from one occasion to the next.

The powder compositions of the present invention may be prepared by a process which comprises mixing the components of the composition including an optional granulation step. The tablets of the present invention may be prepared by compressing the mixture so obtained.

The term "water-insoluble" denotes a hydrophilic polymer that, in powder form, has little or no solubility in water at ambient temperatures under the conditions of use of the compositions of the present invention.

Suitable hydrophilic polymers include starch, for example maize starch; cellulose for example powdered cellulose and microcrystalline cellulose; water-insoluble modified starches for example sodium carboxymethyl starch; water-insoluble cellulose derivatives, for example croscarmellose sodium (cross-linked sodium carboxymethyl cellulose); cross-linked polyvinylpyrrolidone and alginic acid. A preferred hydrophilic polymer is microcrystalline cellulose, for example the products sold as Avicel PH-101 and Avicel PH-102 (Avicel is a Trade Mark) by the FMC Corporation of Philadelphia, Pa., USA. Another preferred hydrophilic polymer is a croscarmellose sodium, for example the product sold as Ac-Di-Sol (Ac-Di-Sol is a Trade Mark) by the FMC Corporation.

Two or more water-insoluble hydrophilic polymers may be incorporaed in the compositions of the present invention. A preferred mixture is croscarmellose sodium and microcrystalline cellulose, for example in the ratio (parts by weight) of 1:10 to 10:1. More preferred is a mixture of 1 part croscarmellose sodium to 1–10 parts, preferably 3–7 parts and especially 5 parts of microcrystalline cellulose.

The surfactant used in the compositions of the present invention is preferably anionic or non-ionic. The surfactant preferably has an HLB (hydrophiliclipophilic balance) value greater than 10.0, for example greater than 12.0 and more particularly greater than 13.0. The surfactant may be a solid or liquid and a single surfactant or more than one surfactant may be used.

Suitable anionic surfactants include sodium lauroylsarcosinate and sodium lauryl sulphate. A preferred anionic surfactant is sodium lauryl sulphate, which is a solid material.

Preferred nonionic surfactants include ethoxylated lauric esters of polyhydric alcohols, for example, polyoxyethylene glycol monolaurates with 4–20 ethylene oxide units per molecule and polyoxyethylene sorbitan monolaurates with 4–20 ethylene oxide units per molecule. One example is Tween 20 (Tween is a Trade Mark), which is a liquid polyoxyethylene sorbitan monolaurate with 20 ethylene oxide units per molecule, available from Atlas Chemical Industries (UK) Ltd. of Leatherhead, United Kingdom.

Pharmaceutically acceptable effervescent couples that produce carbon dioxide in the presence of water are well known in the art. One component of the effervescent couple is suitably a pharmaceutically acceptable solid acid, for example a solid organic acid such as citric acid, tartaric acid, adipic acid or malic acid. One or more acids may be used. The other component of the effervescent couple is suitably sodium carbonate, sodium bicarbonate, potassium carbonate or potassium bicarbonate, or a mixture thereof. The amounts of the components of the effervescent couple are generally chosen so that the pH of the aqueous mixture that results when the compositions of the present invention are added to water is below 7.0, preferably between 3.0 and 5.0 and especially between 3.0 and 4.0.

It has been found that the incorporation of a saccharide in the compositions of the present invention improves the stability of the compositions and gives compositions with an improved shelf life. Thus especially preferred compositions of the present invention are those which comprise a saccharide dispersed therein. Suitable saccharides include, for example, sucrose, lactose, dextrose and sorbitol. Lactose and sucrose are preferred saccharides. Sucrose is especially preferred.

It is preferred to incorporate the saccharide in finely powdered form into the compositions of thepresent invention. The amount of saccharide used is generally within the range of 0.5 to 20, preferably 1 to 10 and especially 4 to 7 parts by weight of saccharide to 1 part by weight of ibuprofen or salt thereof.

Compositions of the present invention include, for example a pharmaceutical powder or tablet composition comprising ibuprofen or a pharmaceutically acceptable salt thereof, a pharmaceutically acceptable effervescent couple that produces carbon dioxide in the presence of water and a pharmaceutically acceptable surfactant, the ibuprofen or salt thereof being contained in granules comprising a pharmaceutically acceptable water-insoluble hydrophilic polymer.

Preferred compositions of the present invention are those in which the ibuprofen or salt thereof and the hydrophilic polymer are in intimate admixture. Especially preferred are such compositions wherein the ibuprofen or salt thereof is contained in granules comprising a mixture of the ibuprofen or salt thereof and the hydrophilic polymer. Powder compositions are particularly preferred. Preferably the granules contain at least one component of the effervescent couple.

The powder compositions of the present invention may consist entirely of granules containing ibuprofen or salt thereof, a surfactant, a water-insoluble hydrophilic polymer, both components of the effervescent couple and preferably also a saccharide. Such granules may be prepared by methods that are known in the art, for example by a wet granulation process using a non-aqueous solvent.

For example, a mixture of dry powder ingredients comprising ibuprofen or a salt thereof, water-insoluble hydrophilic polymer, both components of the effervescent couple, the surfactant and, preferably also a saccharide is prepared. This mixture of powders is then granulated, for example by treatment with a solution of a binding agent such as polyvinylpyrrolidone in a non-aqueous solvent such as isopropanol. The granules are dried and screened by passing them through an appropriately sized sieve.

However preferred powder compositions of the present invention are granules comprising ibuprofen or salt thereof, a water-insoluble hydrophilic polymer and one component of the effervescent couple, preferably the acid component, these granules being mixed with a separate powder, for example granules, comprising the other component of the effervescent couple. The surfactant may be included in the granules containing the ibuprofen or salt thereof or may be incorporated in the remainder of the composition. The saccharide is preferably included in the granules containing the ibuprofen or salt thereof but may alternatively be included in the remainder of the composition. These compositions are prepared by granulation and mixing processes that are well known in the art. It will be appreciated that, since both components of the effervescent couple are not present in the same granule, aqueous or non-aqueous solvents may be used in a wet granulation process to prepare the granules.

For example, a mixture of dry powder ingredients comprising ibuprofen or a salt thereof, water-insoluble hydrophilic polymer, preferably also a saccharide and one component of the effervescent couple is prepared. The mixture is wet granulated, for example by treatment with a solution of a binding agent such as polyvinylpyrrolidone in a nonaqueous solvent such as isopropanol. The granules are dried, sieved to an appropriate size, and mixed with a dry powder comprising the other component of the effervescent couple, the surfactant and, if desired, one or more flavouring agents.

The compositions of the present invention may contain a salt of ibuprofen, but preferably contain ibuprofen itself. If a water-soluble salt of ibuprofen, for example the sodium or potassium salt, is used, the salt reacts with the acid component of the effervescent couple when the composition is added to water, causing at least some of the ibuprofen to precipitate and thus forming an aqueous suspension of ibuprofen. If a water-insoluble salt of ibuprofen, for example the calcium or aluminium salt, is used, a suspension of this salt is obtained when the composition is added to water.

For use by the the patient, the powder compositions of the present invention are packaged in unit dosage form, for example in sachets made of material that is impervious to water. It will be appreciated that the compositions must be packaged so as to protect them from atmospheric moisture.

The tablet compositions of the present invention may be prepared by compressing a powder composition of the present invention, i.e. a mixture comprising ibuprofen or a pharmaceutically acceptable salt thereof, a pharmaceutically acceptable effervescent couple that produces carbon dioxide in the presence of water, a pharmaceutically acceptable surfactant, a pharmaceutically acceptable water-insoluble hydrophilic polymer and preferably also a saccharide. Conventional tabletting methods may be used. It will be appreciated that the hereinbefore described granulation methods may be utilised prior to compressing the mixture into tablets. It may be desirable to incorporate conventional tablet excipients for example a binding agent, for example polyvinylpyrrolidone and/or a lubricant, for example polyethylene glycol 6000 in the powder composition prior to tabletting. It will be appreciated that the tablets of the present invention must be protected from atmospheric moisture. This can be done, for example, by packaging the tablets in individual compartments in a cold-formed blister pack or foil strip.

The compositions of the present invention in unit dosage form suitably contain 50–1200 mg, more usually 200–800 mg ibuprofen or the therapeutic equivalent of a pharmaceutically acceptable salt of ibuprofen.

The compositions of the present invention suitably contain, per 100 parts (parts by weight) ibuprofen or pharmaceutically acceptable salt thereof, 5–100 parts, preferably 10–50 parts and especially 20–40 parts of water-insoluble hydrophilic polymer and 0.01–20 parts surfactant and preferably also 50–2000, especially 100–1000 parts of saccharide. In the case of an anionic surfactant, the preferred amount is 0.01–10 parts, especially 0.1–1.0 parts. In the case of a nonionic surfactant, the preferred amount is 0.1–20 parts, especially 0.5–10 parts.

The following non-limitative Examples illustrate the invention.

EXAMPLE 1

A powder composition was prepared from the following ingredients.

| Ingredient | Weight in grams |
| --- | --- |
| Ibuprofen B.P. | 1575.0 |
| Microcrystalline cellulose[a] | 375.0 |
| Croscarmellose sodium[b] | 75.0 |
| Polyvinylpyrrolidone[c] | 100.0 |
| Malic acid B.P. | 4125.0 |
| Sodium saccharin B.P. | 62.5 |
| Sodium bicarbonate B.P. coarse granules | 2250.0 |
| Anhydrous sodium carbonate | 375.0 |
| Sodium lauryl sulphate B.P. | 7.5 |
| Flavour | 350.0 |
| Isopropanol | q.s |
| Purified water B.P. | q.s |

[a] Avicel PH-101
[b] Ac-Di-Sol
[c] Plasdone K29-32 supplied by GAF (Great Britain) Ltd., of Manchester, UK.

The ibuprofen, microcrystalline cellulose, croscarmellose sodium and malic acid were deaggregated by passage through a 16 mesh sieve and blended in a mixer. To a solution of the polyvinylpyrrolidone in isopropanol (500 ml) was added a solution of the sodium saccharin in purified water B.P. (100 ml). This liquid was used to granulate the powder mixture described above, more isopropanol added as required. The wet granulate was passed through a 4 mesh sieve and dried in a stream of warm air in a fluid bed dryer to a water content less than 0.3% w/w. The dried granules were screened through a 30 mesh sieve and blended with the sodium bicarbonate, anhydrous sodium carbonate, sodium lauryl sulphate and orange flavour to give a uniform mixture. Before blending, the sodium bicarbonate was screened through a 30 mesh sieve whereas the anhydrous sodium carbonate, sodium lauryl sulphate and orange flavour were screened through a 60 mesh sieve. All sieve sizes referred to are British Standard sizes. The resulting powder mixture was packed into water-impervious sachets each containing 630 mg ibuprofen.

The packed sachets were subjected to a storage test at 40° C. After 1 day at this temperature the powder composition had become agglomerated and sticky. Thus the composition was unsatisfactory after storage for 1 day at 40° C.

EXAMPLE 2

A powder composition was prepared from the following ingredients.

| Ingredient | Parts by weight |
| --- | --- |
| Ibuprofen B.P. | 600 |
| Microcrystalline cellulose(a) | 150 |
| Croscarmellose sodium(b) | 30 |
| Sucrose fine powder | 3500 |
| Polyvinylpyrrolidone(c) | 10 |
| Malic acid granular | 1650 |
| Sodium saccharin B.P. | 25 |
| Sodium Bicarbonate B.P. coarse granules | 500 |
| Anhydrous sodium carbonate | 150 |
| Sodium lauryl sulphate B.P. | 3 |
| Orange Flavour | 140 |

(a)Avicel PH-101
(b)Ac-Di-Sol
(c)Plasdone K29-32

The ibuprofen, microcrystalline cellulose, croscarmellose sodium, malic acid, sucrose were deaggregated by passage through a 16 mesh sieve and blended together with the sodium saccharin in a mixer. The mixture was granulated with a solution of the polyvinylpyrrolidone in isopropanol. The resulting granules were dried, screened through a 30 mesh sieve and blended with the remaining ingredients to give a uniform mixture. Before blending, the sodium bicarbonate was screened through a 30 mesh sieve whereas the anhydrous sodium carbonate, sodium lauryl sulphate and orange flavour were screened through a 60 mesh sieve. All sieve sizes referred to are British Standard sizes. The resulting powder mixture was packed into water-impervious sachets each containing 600 mg ibuprofen. The composition was examined after five months storage in a water-impervious closed container at 30° C. and 40° C. and found to be satisfactory.

EXAMPLE 3

A powder composition was prepared from the following ingredients.

| Ingredient | Parts by weight |
| --- | --- |
| Ibuprofen sodium salt dihydrate | 807 |
| Microcrystalline cellulose(a) | 150 |
| Croscarmellose sodium(b) | 30 |
| Polyvinylpyrrolidone(c) | 40 |
| Malic acid granular | 1650 |
| Sodium saccharin B.P. | 25 |
| Sodium bicarbonate B.P. coarse granules | 900 |
| Anhydrous sodium carbonate | 150 |
| Sodium lauryl sulphate B.P. | 3 |
| Orange Flavour | 140 |

(a)Avicel PH-101
(b)Ac-Di-Sol
(c)Plasdone K29-32

In a similar manner to that described in Example 2, granules were prepared containing the ibuprofen sodium salt, microcrystalline cellulose, croscarmellose sodium, malic acid and sodium saccharin. In a similar manner to that described in Example 2, these granules were blended with the remaining ingredients and the resulting mixture was packed into water-impervious sachets each containing 800 mg ibuprofen sodium salt. In a storage test of the sachets at 30° C., the composition was found to be satisfactory after 85 days In storage tests at 40° C., the composition was found to be satisfactory after 40 days but unsatisfactory thereafter, as shown by agglomeration of the powder composition.

EXAMPLE 4

Power formulations were prepared as described in Example 2, except that the sucrose in the formulation was replaced with the same quantity of one of the following saccharides in the form of a fine powder.
 (a) lactose B.P.
 (b) dextrose monohydrate b.p.
 (c) sorbitol The resulting powder formulations were packed into water-impervious closed containers and subjected to storage tests at 30° C. and 40° C. The following results were obtained.

| Composition | Time in months(m) or days(d) at which composition became unsatisfactory at temperature | |
| --- | --- | --- |
| | 30° C. | 40° C. |
| (a) | >3 m | >3 m |
| (b) | >24 d <3 m | >24 d <3 m |
| (c) | >24 d <3 m | 17 d |

The result >3 m signifies that the formulation was satisfactory when examined after 3 months. The result >24 d<3 m signifies that the composition was satisfactory when examined at 24 days but unsatisfactory (agglomeration of powder to a sticky solid) when examined after 3 months.

EXAMPLE 5

Powder formulations were prepared as described in Example 2, except that the amount of sucrose in the formulation was altered to the following amounts.
 (a) 630 parts weight
 (b) 6300 parts weight.

The resulting formulations were packed into water-impervious closed containers and subjected to storage tests at 30° C. and 40° C. The following results were obtained.

| Composition | Time in months(m) or days(d) at which composition became unsatisfactory at temperature | |
| --- | --- | --- |
| | 30° C. | 40° C. |
| (a) | >3 m | 24 d |
| (b) | >24 d <3 m | >24 d <3 m |

EXAMPLE 6

A powder formulation was prepared as described in Example 2, except that the sucrose powder was not included in the granules but was blended with the remaining ingredients after granulation. The resulting formulation was packed into a water-impervious closed container and was subjected to storage tests at 30° C. and 40° C. and the composition was found to be satisfactory after 3 months storage at these temperatures.

EXAMPLE 7

A powder composition is prepared from the following ingredients.

| Ingredient | Parts by weight |
| --- | --- |
| Ibuprofen | 600 |
| Maize starch B.P. | 150 |
| Malic acid granular | 1650 |
| Sodium saccharin | 18 |
| Polyvinylpyrrolidone(a) | 40 |
| Empilan AQ 100(b) | 10 |
| Sodium bicarbonate | 900 |
| Anhydrous sodium carbonate coarse granules | 150 |
| Orange Flavour | 140 |

(a)Plasdone K29-32
(b)A polyoxyethylene glycol monolaurate from Albright and Wilson Ltd. of Whitehaven, Cumbria, U.K.

In a similar manner to that described in Example 1, a mixture of the ibuprofen, maize starch and malic acid is granulated with a solution of the sodium saccharin and polyvinylpyrrolidone in aqueous isopropanol. The granules are dried and blended with the remaining ingredients. The mixture is packed into water-impervious sachets each containing 600 mg ibuprofen.

EXAMPLE 8

A powder composition is prepared as described in Example 7 except that the maize starch is replaced by the same amount of microcrystalline cellulose (Avicel PH-101). The resulting powder is packed into water-impermeable sachets each containing 600 mg ibuprofen.

EXAMPLE 9

A powder composition is prepared from the following ingredients.

| Ingredient | Parts by weight |
| --- | --- |
| Ibuprofen B.P. | 300 |
| Microcrystalline cellulose(a) | 75 |
| Croscarmellose sodium(b) | 15 |
| Sucrose fine powder | 1750 |
| Malic acid granular | 825 |
| Sodium saccharin B.P. | 12.5 |
| Polyvinylpyrrolidone(c) | 5 |
| Sodium bicarbonate B.P. coarse granules | 450 |
| Anhydrous sodium carbonate | 75 |
| Orange Flavour | 70 |
| Sodium lauryl sulphate | 1.5 |

(a)Avicel PH-101
(b)Ac-Di-Sol
(c)Plasdone K29-32

The method used is similar to that described in Example 2. Granules are prepared containing the ibuprofen, microcrystalline cellulose, croscarmellose sodium, malic acid, sucrose sodium saccharin and polyvinylpyrrolidone. The resulting granules are blended with the remaining ingredients and the mixture is compressed into tablets containing 300 mg ibuprofen. The tablets are packed into water-impervious foil strips.

We claim:

1. A pharmaceutical composition in powder or tablet form comprising
   (a) a granular component comprising an intimate mixture of
     (i) 100 parts of ibuprofen or a pharmaceutically acceptable salt thereof;
     (ii) 5–100 parts of a pharmaceutically acceptable water-insoluble hydrophilic polymer; and
     (iii) a pharmaceutically acceptable solid acid forming a first part of an effervescent couple that produces carbon dioxide in the presence of water;
   (b) 0.01 to 20 parts of a pharmaceutically acceptable anionic or non-ionic surfactant;
   (c) a second part of the effervescent couple selected from the group consisting of sodium carbonate, sodium bicarbonate, potassium carbonate, potassium bicarbonate and mixtures thereof, the amounts of the first and second parts of the effervescent couple being such that when the pharmaceutical composition is added to water, the resulting pH is below 7, and
   (d) 400 to 700 parts of a saccharide selected from the group consisting of sucrose and lactose.

2. A pharmaceutical composition according to claim 1 wherein the pharmaceutically acceptable water-insoluble hydrophilic polymer is selected from the group consisting of microcrystalline cellulose, cross-linked sodium carboxymethyl cellulose and mixtures thereof.

3. A pharmaceutical composition according to claim 2 wherein the pharmaceutically acceptable water-insoluble hydrophilic polymer is a mixture of croscarmellose sodium and microcrystalline cellulose in the ratio by weight of 1:10 to 10:1.

4. A pharmaceutical composition according to claim 3 wherein the mixture comprises 1 part croscarmellose sodium to 1 to 10 parts microcrystalline cellulose.

5. A pharmaceutical composition according to claim 4 wherein the mixture comprises 1 part croscarmellose sodium 3 to 7 parts microcrystalline cellulose.

6. A pharmaceutical composition according to claim 1 wherein the pharmaceutically acceptable surfactant is sodium lauryl sulphate or a polyoxyethlene sorbitan monolaurate having 4 to 20 ethylene oxide units per molecule.

7. A pharmaceutical composition according to claim 1 wherein the saccharide is sucrose.

8. A pharmaceutical composition in powder or tablet form comprising
   (a) a granular component comprising an intimate mixture of
      (i) 100 parts of ibuprofen or a pharmaceutically acceptable salt thereof;
      (ii) 5-100 parts of a pharmaceutically acceptable water-insoluble hydrophilic polymer;
      (iii) a pharmaceutically acceptable solid acid forming a first part of an effervescent couple that produces carbon dioxide in the presence of water; and
      (iv) 400 to 700 parts of a saccharide selected from the group consisting of lactose and sucrose;
   (b) 0.01 to 20 parts of a pharmaceutically acceptable anionic or non-ionic surfactant;
   (c) a second part of the effervescent couple selected from the group consisting of sodium carbonate, sodium bicarbonate, potassium carbonate, potassium bicarbonate and mixtures thereof, the amounts of the first and second parts of the effervescent couple being such that when the pharmaceutical composition is added to water, the resulting pH is below 7.

9. A pharmaceutical composition according to claim 8 wherein the pharmaceutically acceptable water-insoluble hydrophilic polymer is selected from the group consisting of microcrystalline cellulose, cross-linked sodium carboxymethyl cellulose and mixtures thereof.

10. A pharmaceutical composition according to claim 9 wherein the pharmaceutically acceptable water-insoluble hydrophilic polymer is a mixture of croscarmellose sodium and microcrystalline cellulose in the ratio by weight of 1:10 to 10:1.

11. A pharmaceutical composition according to claim 10 wherein the mixture comprises 1 part croscarmellose sodium to 1 to 10 parts microcrystalline cellulose.

12. A pharmaceutical composition according to claim 11 wherein the mixture comprises 1 part croscarmellose sodium to 3 to 7 parts microcrystalline cellulose.

13. A pharmaceutical composition according to claim 8 wherein the pharmaceutically acceptable surfactant is sodium lauryl sulphate or a polyoxyethlene sorbitan monolaurate having 4 to 20 ethylene oxide units per molecule.

14. A pharmaceutical composition according to claim 8 wherein the saccharide is sucrose.

* * * * *